(12) United States Patent
Furukawa (10) Patent No.: US 7,108,687 B2
(45) Date of Patent: Sep. 19, 2006

(54) MEDICAL SYSTEM

(75) Inventor: Nobuyuki Furukawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 13 days.

(21) Appl. No.: 10/664,748

(22) Filed: Sep. 18, 2003

(65) Prior Publication Data

US 2004/0204627 A1    Oct. 14, 2004

(30) Foreign Application Priority Data

Sep. 19, 2002    (JP) .............................. 2002-273567

(51) Int. Cl.
*A61B 17/00*    (2006.01)
(52) U.S. Cl. .......................... 606/1; 600/101; 600/109; 600/118; 348/65; 348/68; 348/69; 348/70; 348/71; 348/74
(58) Field of Classification Search ................ 600/101, 600/109, 118; 606/1; 348/74, 65, 68–71
See application file for complete search history.

(56) References Cited

U.S. PATENT DOCUMENTS 5,061,994 A * 10/1991 Takahashi .................... 348/74
5,196,928 A * 3/1993 Karasawa et al. ............ 348/65
5,287,264 A    2/1994 Arita et al.
6,224,542 B1    5/2001 Chang et al.
6,791,601 B1 * 9/2004 Chang et al. ................ 348/65

FOREIGN PATENT DOCUMENTS

JP    6-114065    4/1994

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

An endoscope surgery system is provided, as a medical system, to be easily used by a user who is not used to the operation. An endoscope operation system includes a trolley and a remote controller. The trolley includes a plurality of medical devices (having a TV camera for an endoscope, a light source device, pneumoperitoneum equipment, an electric knife, and a VTR). Further, the trolley includes a system controller for radio communication with the medical devices, and an operation panel and a display panel for operating the system controller. The system controller detects operation states of the plurality of medical devices, determines the medical device to be operated next based on the detection result, and displays, on the operation panel or the display panel, an operation screen of the medical device or a screen for information on the operation state based on the determination result.

4 Claims, 11 Drawing Sheets

| PNEUMOPERITONEUM EQUIPMENT | ELECTRIC KNIFE | |
|---|---|---|
| SETTING FLOW VOLUME 10 ml/min<br>SETTING PRESSURE 10 mmHg | INCISION OUTPUT 100W<br>COAGULATION OUTPUT 80W | 93 |
| (image 92) | TV CAMERA RED TONE +2 | 94 |
| | TV CAMERA BLUE TONE −1 | 95 |
| | LIGHT SOURCE BRIGHTNESS +3 | 96 |
| | LIGHT SOURCE EMERGENCY LAMP OFF | 97 |
| | VTR RECORDING | 98 |

FIG.10

| PNEUMOPERITONEUM EQUIPMENT | ELECTRIC KNIFE | |
|---|---|---|
| SETTING FLOW VOLUME 10 ml/min<br>SETTING PRESSURE 10 mmHg | INCISION OUTPUT 100W<br>COAGULATION OUTPUT 80W | 113 |
| (image 112) | ELECTRIC KNIFE INCISION MODE UROLOGY | 114 |
| | ELECTRIC KNIFE COAGULATION MODE SPRAY | 115 |
| | LIGHT SOURCE BRIGHTNESS +3 | 116 |
| | LIGHT SOURCE EMERGENCY LAMP OFF | 117 |
| | VTR RECORDING | 118 |

MEDICAL SYSTEM

This application claims benefit of Japanese Application No. 2002-273567 filed Sep. 19, 2002, the contents of which are incorporated by this reference.

BACKGROUND OF THE INVENTION

1. Field of the Invention

The present invention relates to a medical system, and more particularly, to a medical system such as an endoscope surgery system having a plurality of medical devices including an endoscope.

2. Description of the Related Art

Recently, medical institutions use a system having a plurality of medical devices.

As one of the above-mentioned systems, Japanese Unexamined Patent Application Publication No. 6-114065 discloses an operation device controlling system which controls the medical devices by previously communicating with them.

In the operation device controlling system disclosed in Japanese Unexamined Patent Application Publication No. 6-114065, a user operates the medical devices on an operation panel. In this case, first, the user selects the medical device to be operated by the operation panel. Next, the user selects a function after selecting the medical device. Sequentially, the user performs the operation of the selected function.

Thus, above three operation steps must be executed to perform a course of operations of the medical device.

Further, in the operation device controlling system disclosed in Japanese Unexamined Patent Application Publication No. 6-114065, first of all, the user selects the medical device and, next, he selects the function. Hence, the user needs sufficient information of the medical devices.

In other words, the operation of the above-mentioned conventional operation device controlling system is extremely hard and complicated for the user who is not used to the system.

SUMMARY OF THE INVENTION

Accordingly, it is an object of the present invention to provide a medical system such as an endoscope surgery system which is easily operated by a user who is not used to the operation thereof.

Briefly, according to the present invention, an endoscope surgery system having a plurality of medical devices including an endoscope, comprises an operation state detecting means which detects operation states of the plurality of medical devices, a device determining means which determines the medical device to be operated next based on a detection result of the operation state detecting means, and a screen control means which displays, on a predetermined display means, an operation screen of the medical device or a screen for information on the operation state of the medical device based on a determination result of the device determining means.

These and other objects and benefits of the present invention will be described in detail and will be apparent.

Further, according to the present invention, in the case of operating one of a plurality of medical devices, a control screen and a screen for setting contents of the medical device are automatically displayed. Therefore, it is possible to provide a medical system such as an endoscope surgery system, in which a medical device is easily operated by a user who is not used to the system.

DESCRIPTION OF THE PREFERRED EMBODIMENTS

Hereinbelow, a description is given of an example of applying the present invention to an endoscope surgery system as a medial system according to embodiments of the present invention.

The endoscope surgery system according to the first embodiment of the present invention will be described hereinafter with reference to FIGS. 1 to 10.

Figure 1:
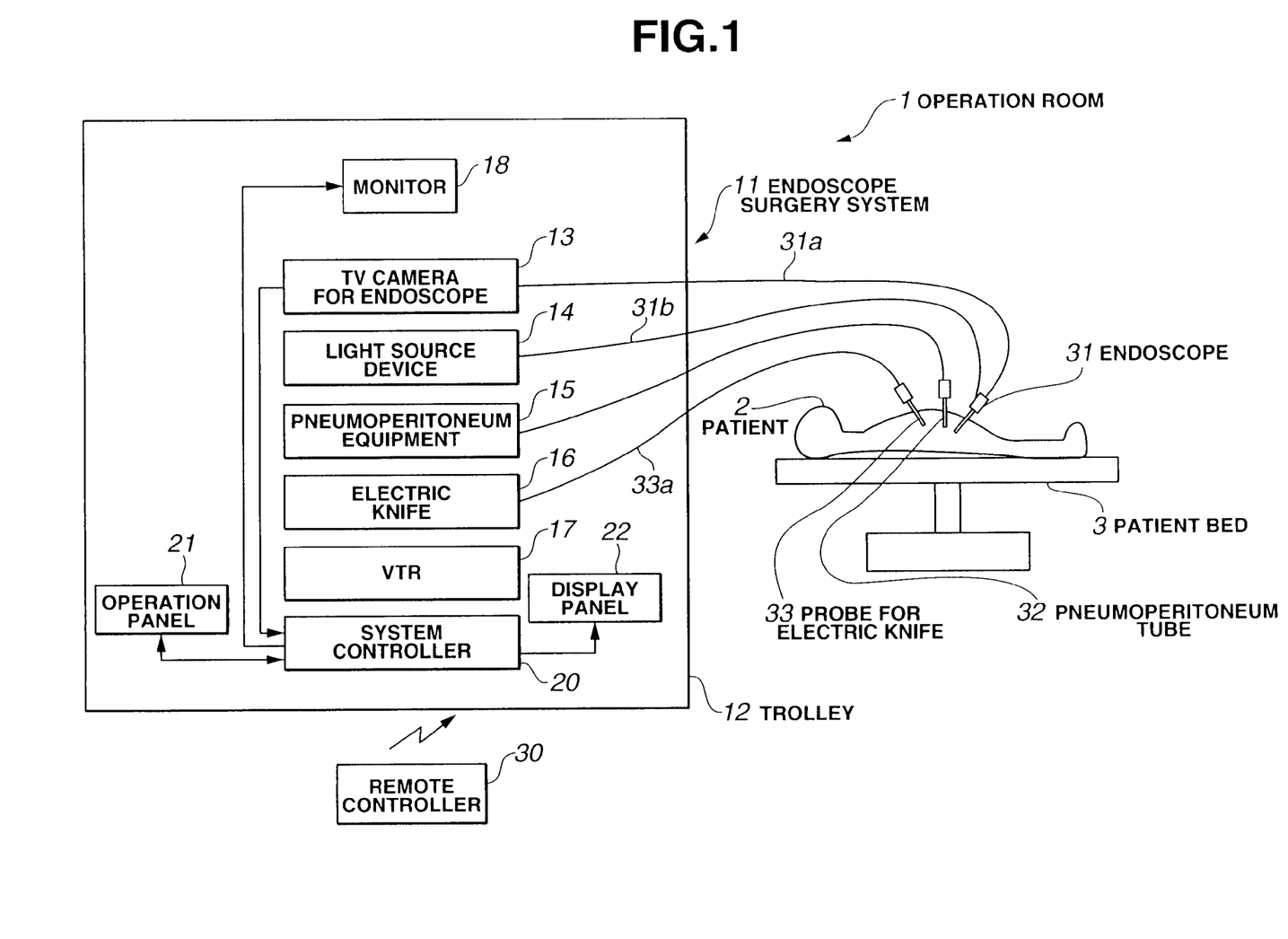
FIG. 1 is an explanatory diagram showing the schematic structure of an endoscope surgery system according to a first embodiment of the present invention.

First, a description is given of the schematic structure of the endoscope surgery system according to the first embodiment with reference to FIG. 1.

Referring to FIG. 1, a patient bed 3 on which a patient 2 lies and an endoscope surgery system 11 are arranged in an operation room 1. The endoscope surgery system 11 comprises a trolley 12 and a remote controller 30.

The trolley 12 comprises a television camera for the endoscope (hereinafter, referred to as a TV camera) 13, a light source device 14, pneumoperitoneum equipment 15, an electric knife 16, and a video tape recorder (hereinafter, referred to as a VTR) 17.

An endoscope 31, a distal side of a pneumoperitoneum tube 32, and a probe 33 for the electric knife are transfixed into the patient 2.

The TV camera 13 for the endoscope is connected to the endoscope 31 via a camera cable 31*a*. The light source device 14 is connected to the endoscope 31 via a light guide cable 31*b*.

A proximal side of the pneumoperitoneum tube 32 is connected to the pneumoperitoneum equipment 15 and receives gas for pneumoperitoneum from the pneumoperitoneum equipment 15.

The probe 33 for the electric knife is connected to a main body of the electric knife 16 via an electric cable 33*a*.

The trolley 12 has a monitor 18 which displays an endoscope image picked up by the TV camera 13 for the endoscope. The VTR 17 records the endoscope image picked up by the TV camera 13 for the endoscope.

The endoscope operation system 11 according to the first embodiment comprises a plurality of medical devices, for example: an endoscope system (also referred to as a first medical device) having the endoscope 31, the camera cable 31*a*, the TV camera 13 for the endoscope, the light source device 14, and the light guide cable 31*b*; an electric knife system (also referred to as a second medical device) having the probe 33 for the electric knife, the electric cable 33*a*, and the electric knife 16; a pneumoperitoneum system having the pneumoperitoneum tube 32 and the pneumoperitoneum equipment 15; and the VTR 17 for recording image data indicating the endoscope image captured by the endoscope system operation system 11 to a predetermined recording medium.

Further, the trolley 12 comprises a system controller 20 for radio communication with the above medical devices, an operation panel 21 for operating the system controller 20, and a display panel 22. The operation panel 21 and the display panel 22 are connected to the system controller 20 via dedicated cables, respectively.

The system controller 20 detects operation states of the plurality of medical devices, determines a predetermined medical device to be operated next based on the detection result, and displays, on the operation panel 21 or the display panel 22, an operation screen of the predetermined medial device to be operated next or a screen for information on the operation state of the predetermined medical device to be operated next based on the determination result.

That is, a signal from the TV camera 13 for the endoscope is received by a control unit 46 via a radio communication unit 45. In accordance with the signal, the control unit 46 detects and determines the operation state of the endoscope system as the first medical device, forecasts the operation to be operated next based on the determination result, and displays, on the operation panel 21 or the display panel 22, the operation screen forecasted as the next operation based on the forecasting result.

For example, a signal from the electric knife 16 is received by the control unit 46 via the radio communication unit 45. In accordance with the signal, the control unit 46 detects and determines the operation state of the electric knife 16 as the second medical device, forecasts the operation to be operated next based on the determination result, and displays, on the operation panel 21 or the display panel 22, the operation screen forecasted as the next operation based on the forecasting result.

Incidentally, the display panel 22 comprises a normal CRT monitor or a liquid crystal display monitor.

Therefore, the control unit 46 in the system controller 20 has a function of a first determining circuit for determining the operation state of the endoscope system (first medical device), a function of a second determining circuit for determining the operation state of the electric knife system (second medical device), and a function of a forecasting circuit for forecasting the next operation based on the determination results of the first determining circuit and the second determining circuit.

The remote controller 30 remotely controls the system controller 20 by infrared.

Figure 2:
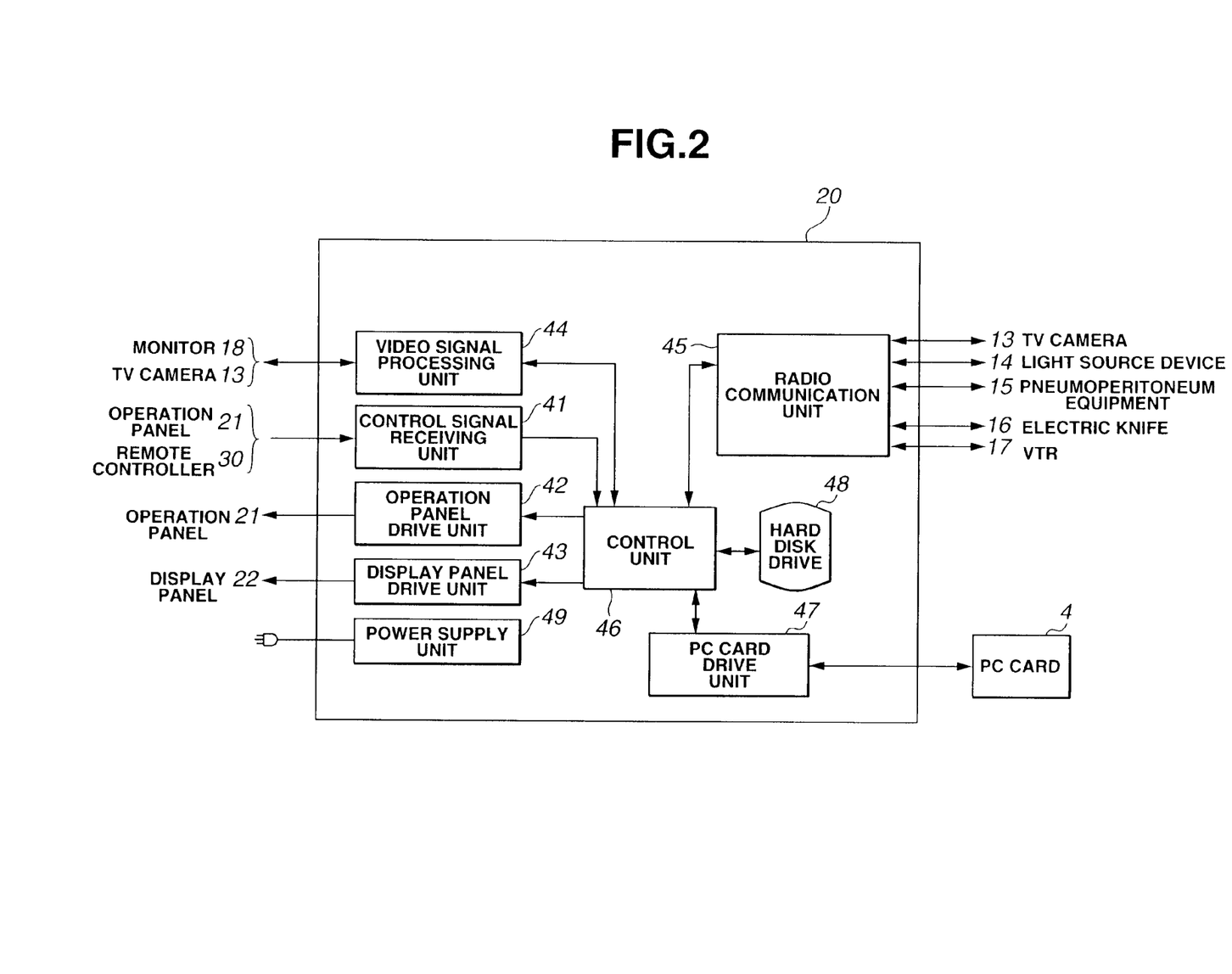
FIG. 2 is a block diagram showing the internal structure of a system controller according to the first embodiment of the present invention.

Next, a description is given of the internal structure of the system controller 20 in the endoscope surgery system according to the first embodiment with reference to FIG. 2.

The system controller 20 comprises: a control signal receiving unit 41; an operation panel drive unit 42; a display panel drive unit 43; a video signal processing unit 44; the radio communication unit 45; the control unit 46; a PC card drive unit 47; a hard disk 48; and a power supply unit 49.

The control unit 46 controls the control signal receiving unit 41, the operation panel drive unit 42, the display panel drive unit 43, the video signal processing unit 44, the radio communication unit 45, the PC card drive unit 47, and the hard disk 48. The power supply unit 49 supplies a desired DC power voltage to the components in the system controller 20.

The control signal receiving unit 41 is operated under the control of the control unit 46, receives the signal from the remote controller 30 or the operation panel 21, converts the received signal to reception data, and supplies the data to the control unit 46.

The operation panel drive unit 42 transmits, to the operation panel 21, information necessary for display on the operation panel 21 under the control of the control unit 46.

The display panel drive unit 43 transmits, to the display panel 22, information necessary for display on the display panel 22 under the control of the control unit 46.

The radio communication unit 45 communicates with the medical devices mounted on the trolley 12 shown in FIG. 1. Thus, the radio communication unit 45 radio-communicates, by IEEE 802.11b or IEEE 802.11g, with the TV camera 13 for the endoscope, the light source device 14, the pneumoperitoneum equipment 15, the electric knife 16, and the VTR 17, under the control of the control unit 46.

The PC card drive unit 47 receives and transmits data to/from an external personal computer, via the PC card 4 under the control of the control unit 46.

The video signal processing unit 44 converts, into a digital video signal, the radio signal of IEEE 802.11a transmitted from the TV camera 13 for the endoscope under the control of the control unit 46, records the signal as a still image to the PC card 4 via the control unit 46 and the PC card drive unit 47, converts the signal into an analog signal again, then, and transmits the signal to the monitor 18 via a cable by using wiring.

The hard disk 48 stores data for automatically setting the control unit 46, reads the stored automatic setting data if necessary, and supplies the data to the control unit 46.

The control unit 46 (in the system controller 20) is operation state detecting means which receives predetermined signals inputted from the TV camera 13 for the endoscope, the light source device 14, the pneumoperitoneum equipment 15, the electric knife 16, and the VTR 17 via the radio communication unit 45 and which detects the operation states of the medical devices.

Further, the control unit 46 (in the system controller 20) is device determining means which determines the predetermined medical device to be operated next based on the detection result of the system controller 20 (as the operation state detecting means).

The operation panel drive unit 42 and the display panel drive unit 43 are screen control means which displays, on the operation panel 21 or the display panel 22 as predetermined display means, the operation screen of the predetermined medical device to be operated next or the screen for the information on the operation state of the predetermined medical device to be operated next, based on the determination result of the control unit 46 (device determining means).

The operation panel drive unit 42 functions as a display circuit which displays, on a predetermined monitor screen, the operation screen to be forecasted as the next operation in accordance with the forecasting result of the control unit 46 (forecasting circuit) of the system controller 20.

Figure 3:
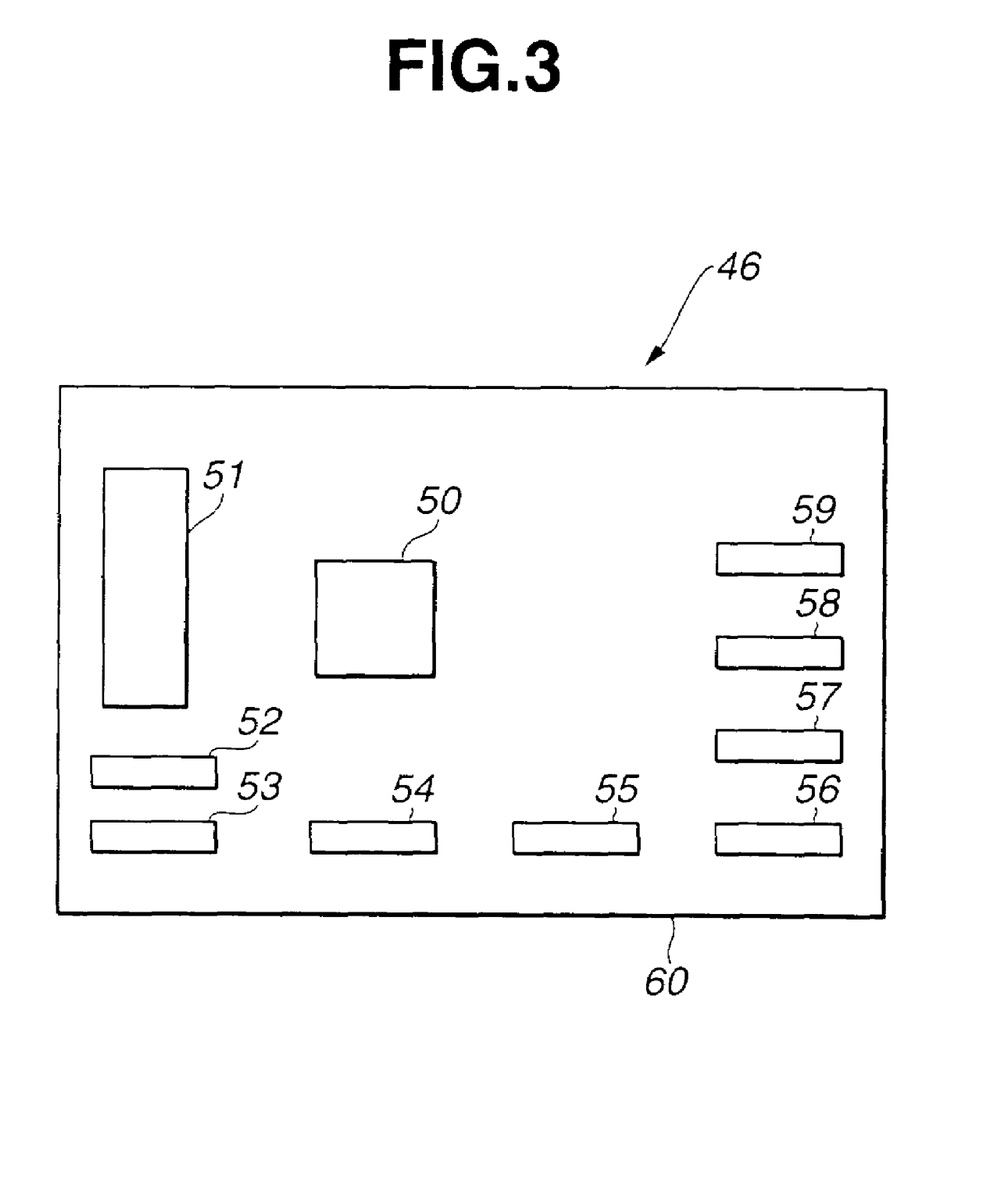
FIG. 3 is an explanatory diagram showing in detail a control unit of the system controller according to the first embodiment of the present invention.

Next, a detailed description is given of the control unit 46 in the system controller 20 in the endoscope surgery system according to the first embodiment with reference to FIG. 3.

Referring to FIG. 3, the control unit 46 is a board personal computer comprising a board 60, and comprises: a CPU 50; a RAM 51; and various general interfaces of the personal computer on the board 60, such as a serial port 52, parallel port 53, a LAN port 54, a PS/2 port 55, a USB port 56, an FDD port 57 of a floppy (R) disk drive, an IDE port 58 of a hard disk drive, and a video port 59 for outputting the video signal.

Figure 4:
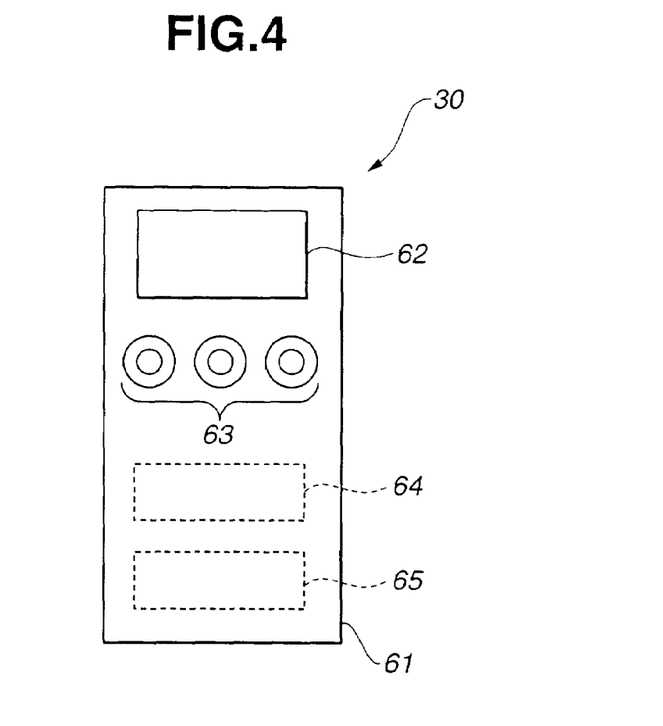
FIG. 4 is a plan view showing a remote controller according to the first embodiment of the present invention.

Next, a detailed description is given of the remote controller 30 in the endoscope surgery system according to the first embodiment with reference to FIG. 4.

Referring to FIG. 4, the remote controller 30 comprises; a casing 61; a display unit 62; an operation button unit 63; a control unit 64; and a transmitting unit 65.

The display unit 62 is arranged on the surface of the casing 61, and displays operated equipment or a function of the remote controller 30. The operation button unit 63 is arranged to the surface of the casing 61 and is pressed by the user.

The casing 61 has the control unit 64 and the transmitting unit 65.

The control unit 64 controls the display unit 62 and the transmitting unit 65 based on the operation of the operation button unit 63. The transmitting unit 65 transmits a radio signal to the system controller 20 or the like shown in FIG. 1 under the control of the control unit 64.

Figure 5:
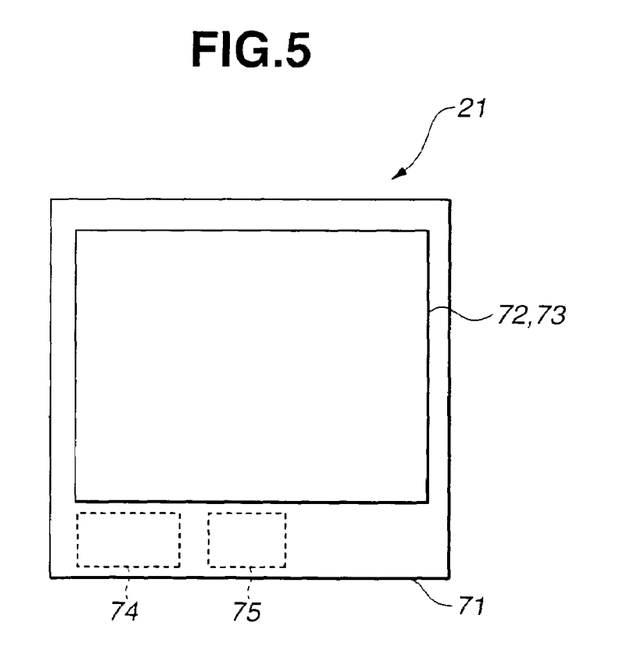
FIG. 5 is a front view showing an operation panel according to the first embodiment of the present invention.

Next, a detailed description is given of the operation panel 21 in the endoscope surgery system according to the first embodiment with reference to FIG. 5.

Referring to FIG. 5, the operation panel 21 controls the medical devices to be operated by a touch panel method.

The operation panel 21 comprises: a casing 71; a liquid crystal display unit (hereinafter, referred to as an LCD unit) 72; a touch panel unit 73; a transmitting unit 74; and a control unit 75.

The LCD unit 72 is arranged to the surface of the casing 71, and displays operated equipment, a function, and an image of the operation button under the control of the control unit 75.

The touch panel unit 73 is overlappingly arranged to the surface of the LCD unit 72 and detects the touch position of the user.

The control unit 75 controls the LCD unit 72 and the transmitting unit 74 based on the operation of the touch panel unit 73. The transmitting unit 74 transmits the operation data to the system controller 20 shown in FIG. 1 under the control of the control unit 75.

As mentioned above, the endoscope surgery system 11 shown in FIG. 1 comprises a plurality of medical devices including the above endoscope 31.

Figure 6:
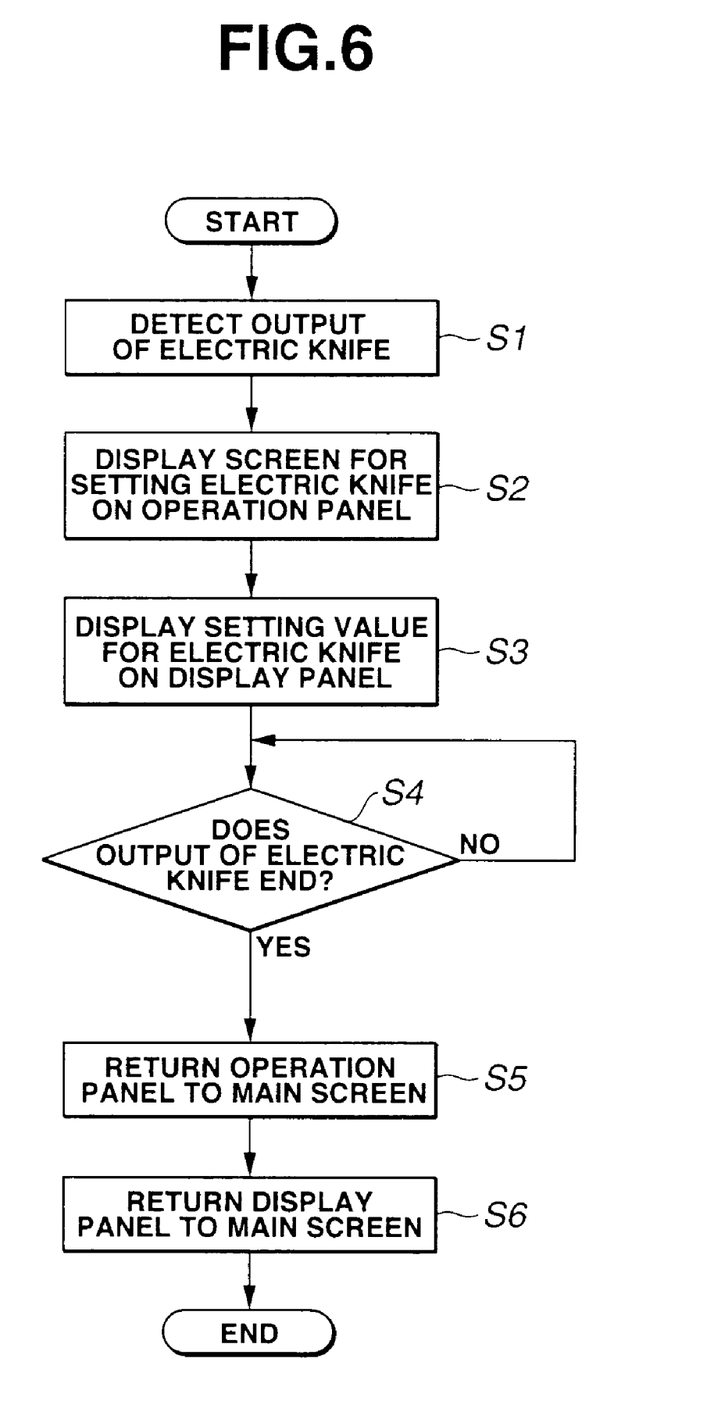
FIG. 6 is a flowchart showing the operation of the system controller according to the first embodiment of the present invention.

A description is given of the operation with the structure according to the first embodiment with reference to a flowchart shown in FIG. 6.

Figure 7:
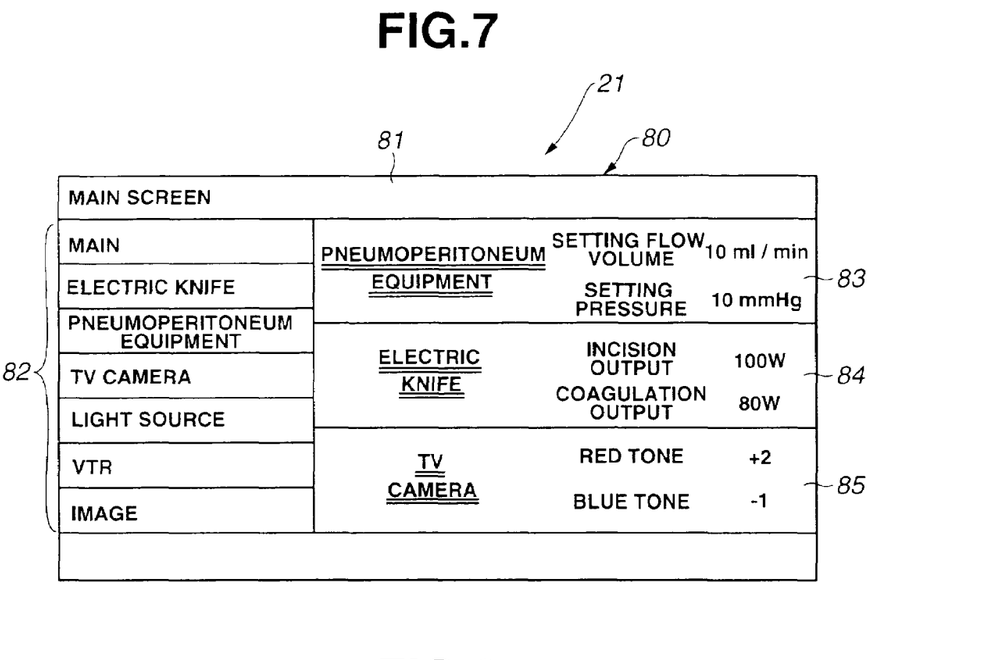
FIG. 7 is an explanatory diagram showing a main screen displayed on the operation panel according to the first embodiment of the present invention.
Figure 8:
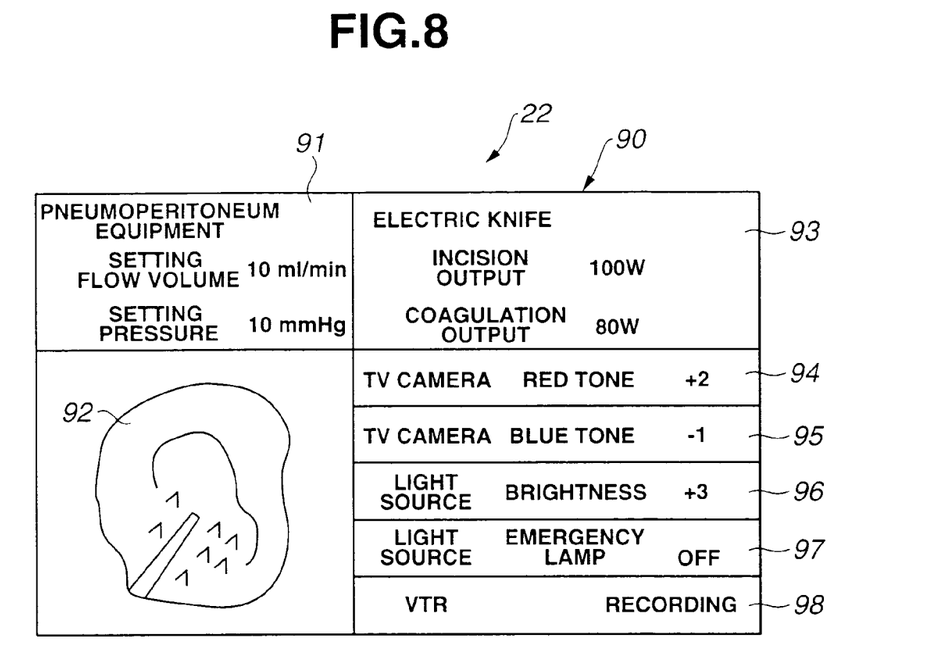
FIG. 8 is an explanatory diagram showing a main screen displayed on a display panel according to the first embodiment of the present invention.

In a normal state of the endoscope surgery system 11, the operation panel 21 displays a main screen 80 shown in FIG. 7, and the display panel 22 displays a main screen 90 shown in FIG. 8.

Hereinbelow, a description is given of the operation for outputting high-frequency current to the probe 33 for the electric knife from the electric knife 16 in the normal state.

The user (operator in this case) presses a foot switch (not shown) of the electric knife 16 and, then, the electric knife 16 outputs the high-frequency current from the edge of the probe 33 for the electric knife. The information is transmitted to the radio communication unit 45 in the system controller 20, and the system controller 20 detects that the electric knife 16 outputs the high-frequency current and recognizes the detection information as information for outputting the electric knife in step S1 in FIG. 6.

Here, the operator of the electric knife 16 continues the using operation if the knife is keen. However, if the knife is not keen as compared with his expectation, he confirms the setting. If the setting is wrong, the operator changes the setting.

Here, the knife is very dull or the desired high-frequency current is not outputted after changing the setting and, then, the operator considers that the electric knife 16 is damaged. Thus, the device is inspected by referring to trouble shooting.

When the system controller 20 recognizes the output state of the electric knife 16, the next action of the operator is considered, such as the confirmation for setting the electric knife 16, the setting change, the reference of the trouble shooting of the electric knife 16.

Figure 9:
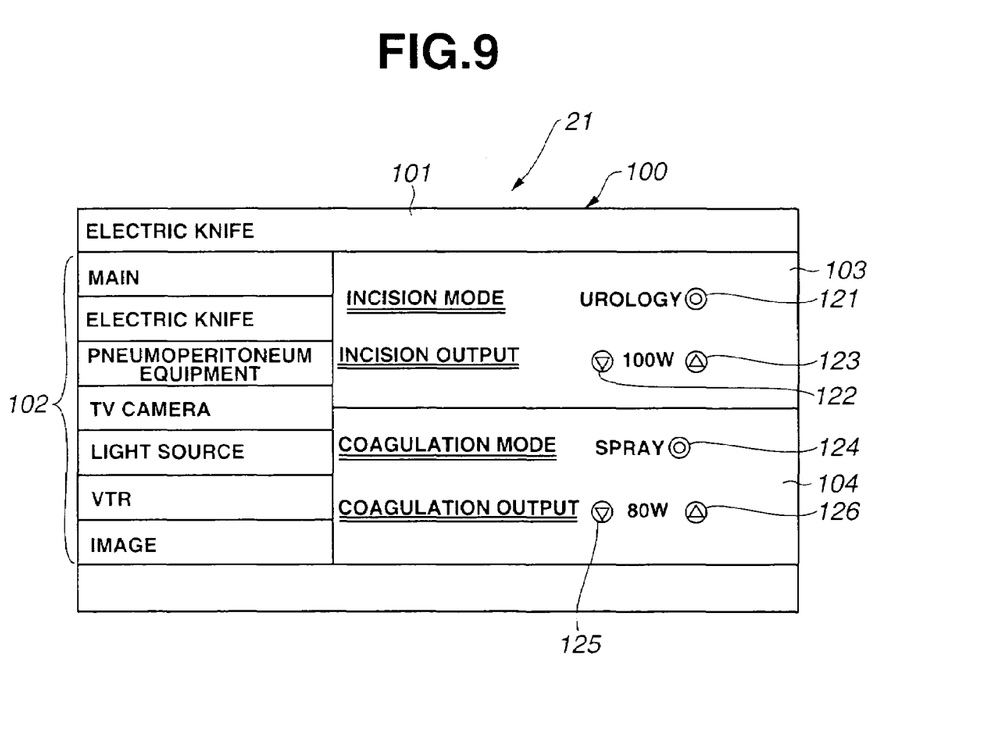
FIG. 9 is an explanatory diagram showing a screen for operating an electric knife displayed on the operation panel according to the first embodiment of the present invention.

In step S2 in FIG. 6, the system controller 20 previously displays an operation screen 100 of the electric knife shown in FIG. 9 on the operation panel 21 based on the above consideration, and further displays setting buttons (buttons 121 to 126) of the electric knife 16 on the operation screen 100 of the electric knife. Next, in step S3 in FIG. 6, the system controller 20 displays a screen 110 for information on the operation state of the electric knife shown in FIG. 10 on the display panel 22, and further displays the setting of the electric knife 16 on the operation screen 110 of the electric knife.

In step S4 in FIG. 6, the system controller 20 repeats the processing in step S4 while the electric knife 16 outputs the high-frequency current. In the case of ending the output of the high-frequency current by the electric knife 16, in step S5 in FIG. 6, the system controller 20 displays the main screen 80 shown in FIG. 7 on the operation panel 21. In step S6 in FIG. 6, the display panel 22 displays the main screen 90 shown in FIG. 8, and the processing ends.

In the flowchart shown in FIG. 6, the display operation of the operation panel 21 and the display panel 22 is returned simultaneously with the end of outputting by the electric knife 16. However, the returning timing may be one minute later after the ending of output.

A detailed description is given of the screens shown in FIGS. 7 to 10.

Referring to FIG. 7, usually, the operation panel 21 displays the main screen 80.

An area 81 on the top of the main screen 80 displays a character indicating the type of screen (main screen).

In the bottom of the area 81 in the main screen 80, an area 82 on the left displays characters of menus for selecting the screen, such as "main", "electric knife", "pneumoperitoneum equipment", . . . , and "image". The operation panel 21 is exchanged by selecting and pressing the characters of the menu.

In the bottom of the area 81 of main screen 80, an area 83 on the right from the middle portion displays setting contents of the pneumoperitoneum equipment 15.

An area 84 on the bottom of the area 83 in the main screen 80 displays the setting contents of the electric knife 16.

An area 85 in the bottom of the area 84 in the main screen 80 displays the setting contents of the TV 13.

Referring to FIG. 8, usually, the display panel 22 displays the main screen 90.

An area 91 on the upper left of the main screen 90 displays the setting contents of the pneumoperitoneum equipment 15.

An area 92 on the down left of the display panel 22 displays the endoscope image picked up by the TV camera 13.

An area 93 on the upper right of the display panel 22 displays the setting contents of the electric knife 16.

The bottom of the area 93 in the display panel 22 displays, in the descending order, an area 94 indicating the setting of a red tone of the TV camera 13, an area 95 indicating the setting of a blue tone of the TV camera 13, an area 96 indicating the setting of brightness of the light source device 14, an area 97 indicating the setting of on/off of an emergency lamp of the light source device 14, and an area 98 indicating the setting of a VTR mode.

When the system controller 20 shown in FIG. 1 recognizes the output of the electric knife 16, referring to FIG. 9, the operation panel 21 displays the operation screen 100 of the electric knife.

An area 101 on the top of the operation screen 100 of the electric knife displays a character indicating the screen type (electric knife).

An area 102 on the left in the bottom of the area 101 in the operation screen 100 of the electric knife displays characters of menus for selecting the screen, such as "main", "electric knife", "pneumoperitoneum equipment", . . . , and "image".

An area 103 on the right from the middle is arranged in the bottom of the area 101 in the operation screen 100 of the electric knife. The area 103 displays the setting contents of an incision mode of the electric knife 16, the button 121 for selecting the incision mode, and the up-button 122 and the down-button 123 of the incision output.

An area 104 on the lower side of the area 103 of the operation screen 100 of the electric knife displays the setting contents of a coagulation mode of the electric knife 16, the button 124 for selecting the coagulation mode, and the up-button 125 and the down-button 126 for a coagulation output.

Figure 10:
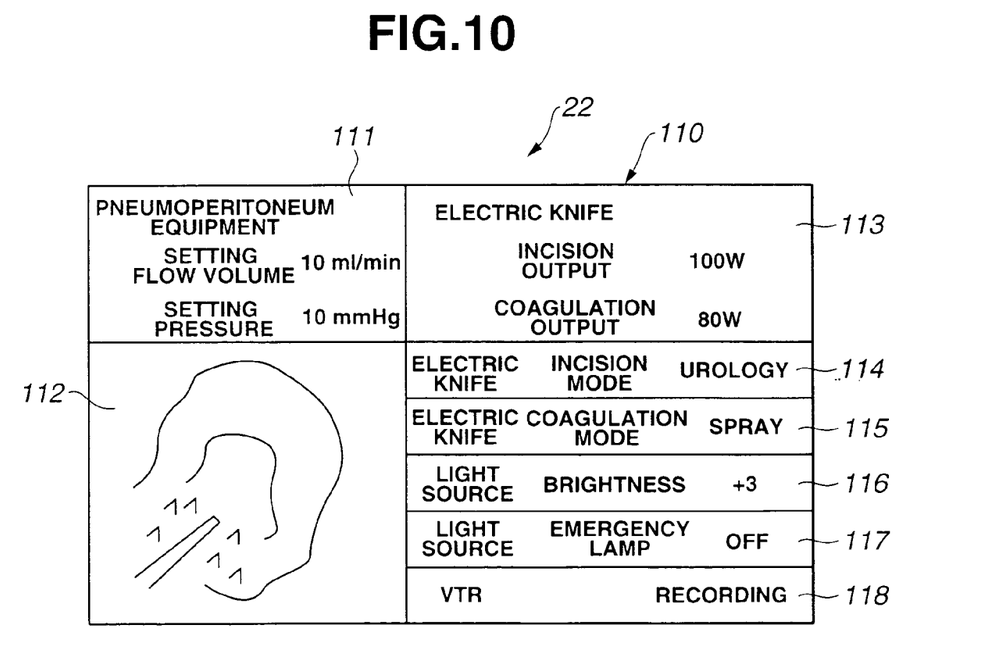
FIG. 10 is an explanatory diagram showing a screen for information on an operation state of the electric knife displayed on the display panel according to the first embodiment of the present invention.

When the system controller 20 shown in FIG. 1 recognizes the output of the electric knife 16, referring to FIG. 10, the display panel 22 displays the screen 110 for the information on the operation state of the electric knife.

An area 111 on the upper left of the screen 110 for the information of the operation state of the electric knife displays the setting contents of the pneumoperitoneum equipment 15.

An area 112 on the down left of the display panel 22 displays the endoscope image picked up by the TV camera 13.

An area 113 on the upper right of the display panel 22 displays the setting contents of the electric knife 16.

The bottom of the area 113 in the display panel 22 displays, in the descending order, an area 114 indicating the setting of the incision mode of the electric knife 16, an area 115 indicating the setting the coagulation mode of the electric knife 16, an area 116 indicating the setting of the brightness of the light source device 14, an area 117 indicating the setting of on/off of the emergency lamp of the light source device 14, and an area 118 indicating the setting of the VTR mode.

As medical processing equipment for heating, coagulating, and incising the body anatomy, an ultrasonic output device is used, in addition to the electric knife 16. According to the first embodiment, upon using the ultrasonic output device, the similar display processing is performed on the operation panel 21 or the display panel 22. In this case, the ultrasonic output device applies ultrasonic vibrations to an edge portion of a clamp, generates the friction heat in the sandwiched body anatomy, and coagulates or incises the anatomy.

According to the first embodiment, a recording device uses, e.g., the VTR 17. The VTR 17 is used for the purpose of recording the endoscope image during the operation.

A video tape as a recording medium used for the VTR 17 is that for two hours, for six hours, or the like. Therefore, upon operation over a recording time, conventionally, the video tape ends in the halfway and only a message indicating such a fact is displayed simultaneously with the end of the video tape. Here, the remaining time of the video tape is known from the VTR 17. Thus, according to the first embodiment, when the remaining time is 10 minutes, a message instructing the exchange of video tape is displayed on the operation panel 21 or the display panel 22 and it is informed to the operator. Further, according to the first embodiment, the operation screen of the VTR 17 is displayed on the operation panel 21.

As the recording device, a video printer device can be used in addition to the VTR. The remaining amount of ink ribbon of the video printer is known from the video printer. Thus, according to the first embodiment, when the remaining amount of ink ribbon of the video printer is 10 pieces, a message instructing the exchange of ink ribbon is informed to the operator on the operation panel 21 or the display panel 22.

According to the first embodiment, a method for exchanging the ink ribbon can be displayed on the screen of the operation panel 21 or the display panel 22.

Further, according to the first embodiment, the following method is considered in addition to the display operation of the medical device.

The system controller 20 has a function for setting, in a lump, the medical devices to setting values which are previously inputted, namely, an automatic setting.

Usually, the automatic setting is performed in a preparing step before the operation. As the operation in the preparing step, the white balance of the TV camera device for the endoscope is adjusted or the recording of the VTR starts.

That is, the system controller 20 displays a white balance screen of the TV camera device for the endoscope on the operation panel 21 or the display panel 22 after completing the automatic setting.

After setting the white balance, the system controller 20 displays the operation panel of the VTR on the operation panel 21 or the display panel 22.

Further, the system controller 20 sequentially displays forecasted operation screens on the operation panel 21 or the display panel 22.

According to the first embodiment, in the endoscope surgery system, the indexes to be operated next are displayed on the operation panel 21 or the display panel 22 from the normal medical action and the preparing action of the operator and, thus, the user who is not used to the operation thereof can easily operate it.

Figure 11:
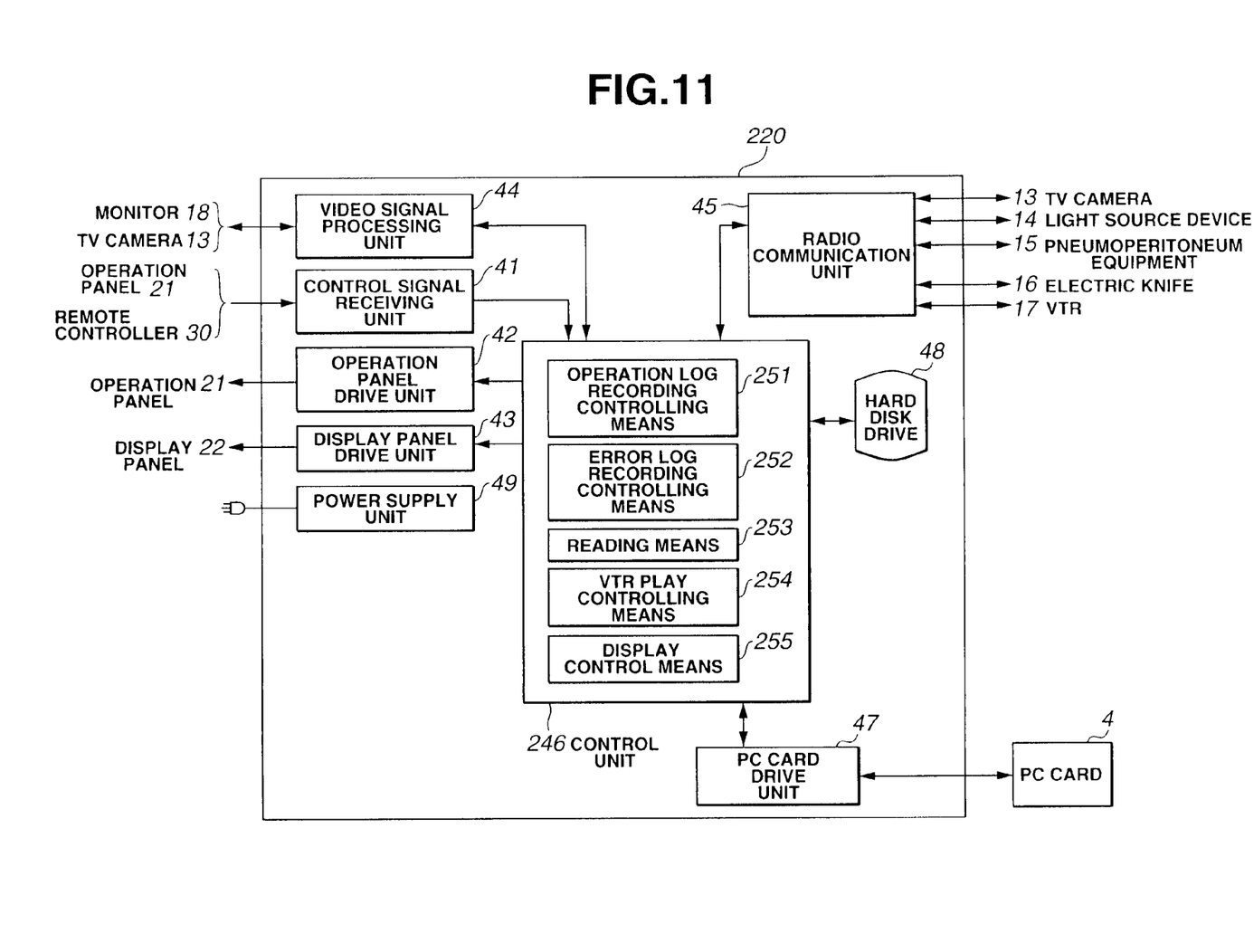
FIG. 11 is a block diagram showing a main portion of a system controller in an endoscope surgery system according to a second embodiment of the present invention.
Figure 12:
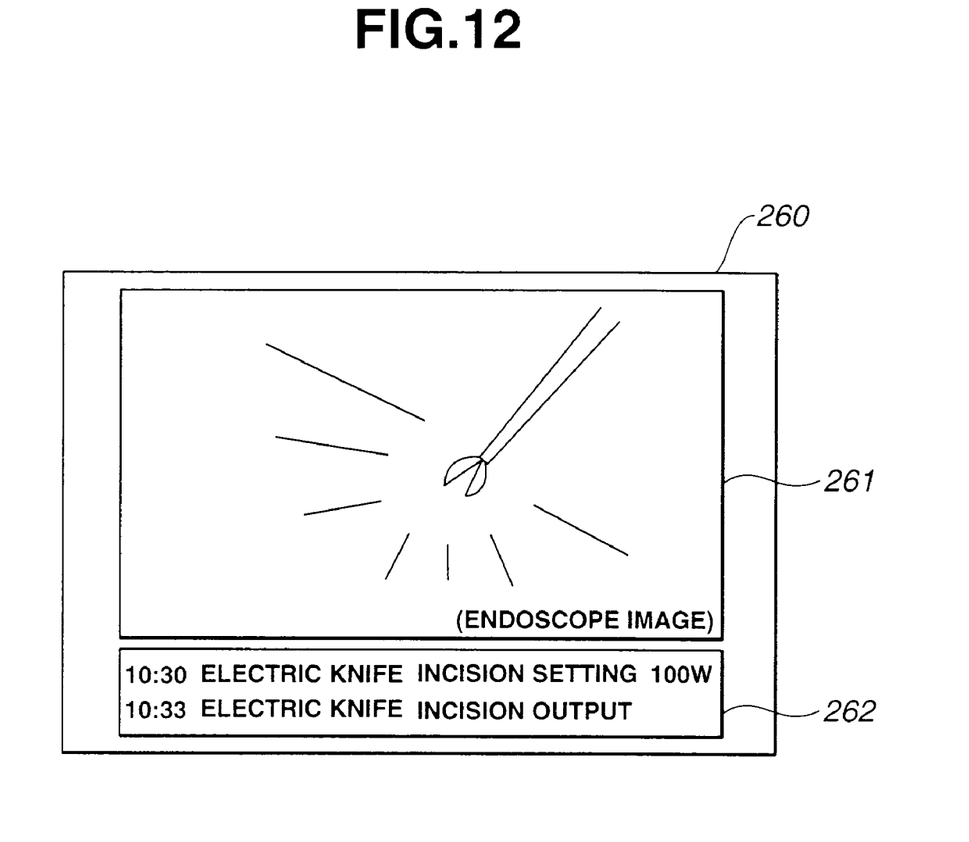
FIG. 12 is an explanatory diagram showing a screen for playing a video tape of a VTR according to the second embodiment of the present invention.

Next, a description is given of an endoscope surgery system according to a second embodiment of the present invention with reference to FIGS. 11 and 12.

Referring to FIG. 11, a system controller 220 comprises: the components of the system controller 20 shown in FIG. 2 according to the first embodiment; and a control unit 246 having operation log recording controlling means 251, error log recording controlling means 252, reading means 253, VTR play controlling means 254, and display control means 255.

When the above medical device is operated, the operation log recording controlling means 251 records the operation contents as an operation log file to the hard disk 48.

When the error is caused in the above medical device, the error log recording controlling means 252 records error contents as an error log file to the hard disk 48.

According to the second embodiment, the VTR 17 has means for recording, to the video tape, time for starting the recording and time for ending the recording.

Thus, with the above-mentioned structure, the operation log recording controlling means 251, the error log recording controlling means 252, and the hard disk 48 are state change recording means which records a state change of the medical device to the log file together with the causing time, when the state of the medical device changes. The VTR 17 is recording means which records the endoscope image.

When the VTR 17 is played, the reading means 253 reads start time and end time of the recording to the video tape (recording medium) of the VTR 17. The recording means 253 reads the recording start time which is recorded to the video tape (recording medium).

Therefore, the reading means 253 is recording-start-time recording means which records the recording start time to the video tape (recording medium).

The VTR play controlling means 254 plays the VTR 17 based on the data from the control signal receiving unit 41.

The VTR play controlling means 254 is play and display means which plays and displays the video image recorded to the VTR 17 (recording means) on the monitor 18 or the display panel 22.

The display control means 255 counts the play time of the VTR 17, calculates the time together with the start time, and displays, on the monitor 18 or the display panel 22, information recorded to the operation log file or the error log file in the hard disk 48 simultaneously with the generated image on the VTR 17.

Therefore, the display control means 255 comprises play counting means, calculating means, and log contents display means.

The play counting means of the display control means 255 counts the play time of the VTR play controlling means 254 (play and display means).

The calculating means of the display control means 255 calculates the actual play time by adding the recording start time read by the reading means 253 and the play counting time by the play counting means.

The log contents display means of the display control means 255 compares the actual play time calculated by the calculating means with the occurrence time of the log file, and displays the log contents at the occurrence time simultaneous with the actual play time.

Conventionally, the operation log and the error log are usually recorded as text information. The operation log and the error log are mainly used by, a service person for maintenance. When the operation log and the error log have the text information, the performed operation and the error index are known. However, the occurrence timing and situation of the performed operation and error are not known.

In addition to the service person, the operator reviews the operation state or reports the operation state to another doctor. However, the occurrence timing and situation are not known.

To solve the difficult operation situations, according to the second embodiment, the operation log, the error log, and the endoscope image are displayed together to easily be viewed.

The medical devices are directly operated, thereby transmitting the information to the system controller 220.

When the medical devices are operated via the operation panel 21, the information is transmitted to the system controller 220.

The operation log recording controlling means 251 in the control unit 246 records the information as the operation log file into the hard disk 48 in the system controller 220.

When the error is caused in the medical devices, similarly to the operation log file, the error information is transmitted to the system controller 220.

The error log recording controlling means 252 in the control unit 246 records the information as the error log file to the hard disk 48 in the system controller 220.

The endoscope image during the operation is generally recorded to the VTR 17. Upon starting to record the data of the VTR 17, the start time and the end time are recorded and are stored in a video tape as a recording medium of the VTR 17.

Recently, the information may be recorded to recording devices such as the hard disk or a DVD device, in place of the VTR.

The above-stored video tape is played and then a screen 260 shown in FIG. 12 is displayed on the monitor 18 or the display panel 22.

The screen 260 comprises a play area 261 of the recording image of the VTR 17, and a display area 262 for the operation log and the error log. Upon playing the VTR 17, the start time recorded to the VTR 17 is read to the reading means 253 and the play counting means in the display control means 255 starts to play and counts the VTR 17. Based on the start time and counting time, the log contents display means of the display control means 255 searches for the operation log and the error log in the hard disk 48, and displays the indexes recorded to the corresponding operation log and error log on the display area 262 for the operation log and the error log.

According to the second embodiment, the operation log, the error log, and the endoscope image are simultaneously displayed. Thus, the information on the operation situation and the error occurrence is easily viewed and the analysis of the device failure and of the operation of the operator is easily performed.

Figure 13:
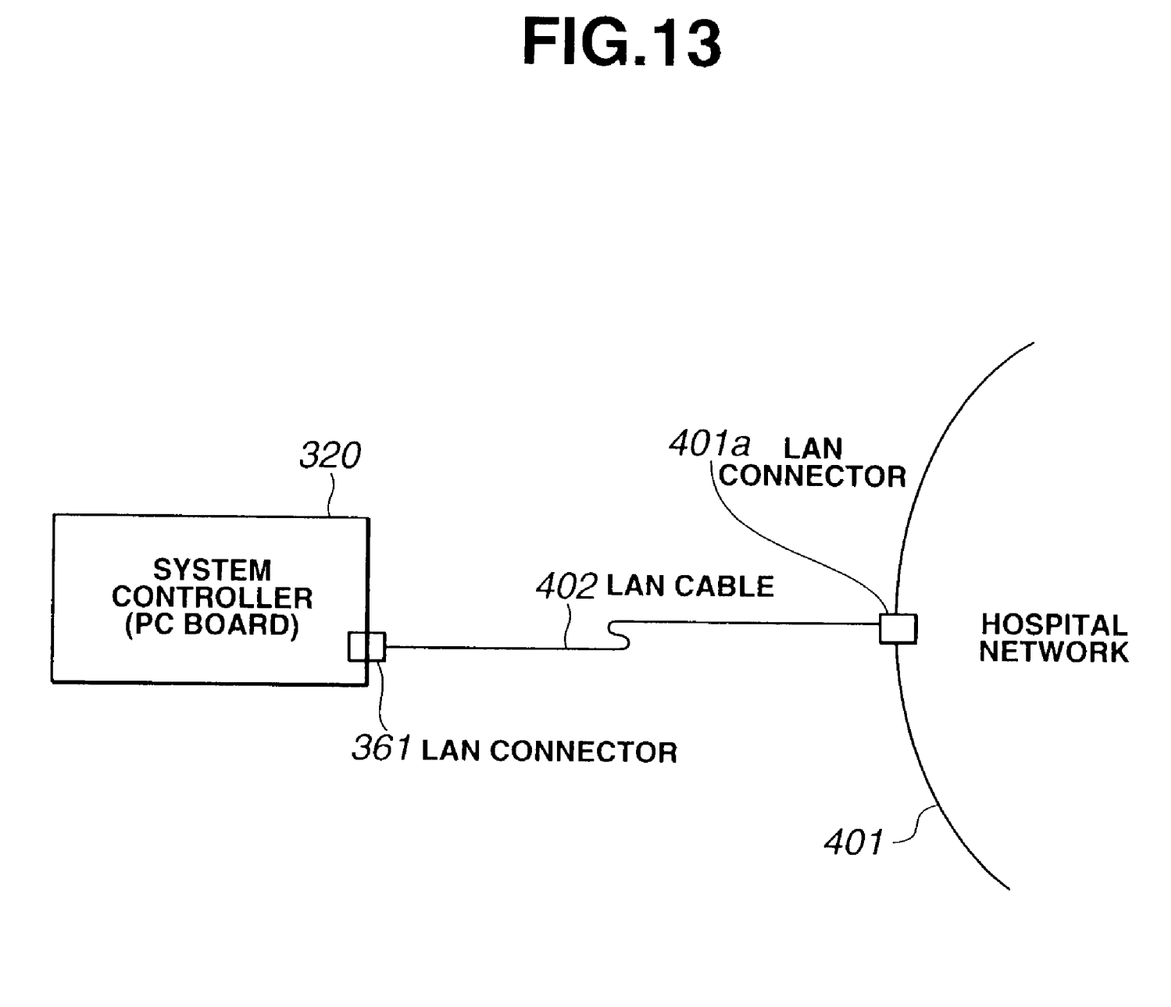
FIG. 13 is an explanatory diagram showing the connection between a system controller and a hospital network according to a third embodiment of the present invention.
Figure 14:
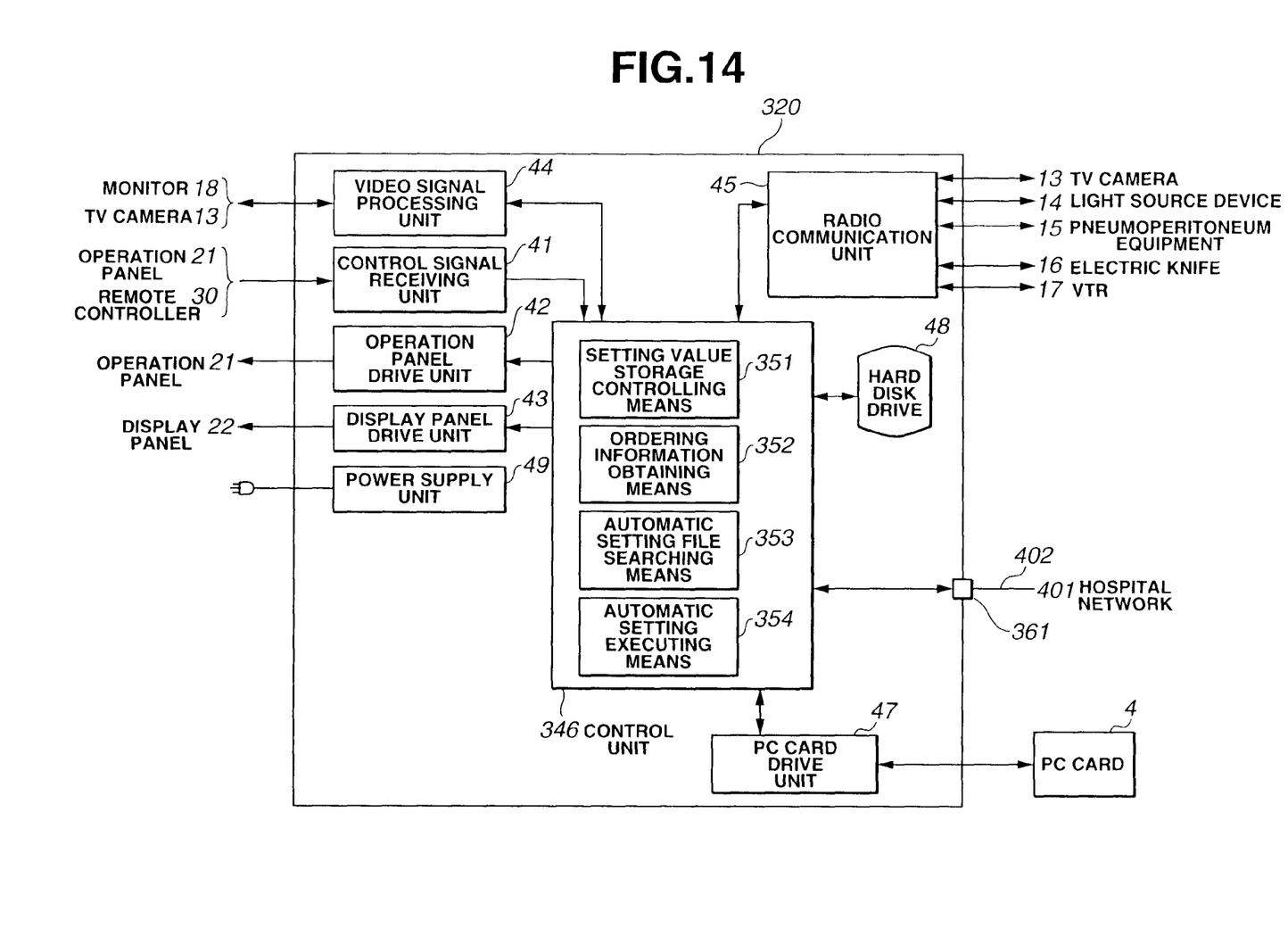
FIG. 14 is a block diagram showing a main portion of the system controller in the endoscope surgery system according to the third embodiment of the present invention.
Figure 15:
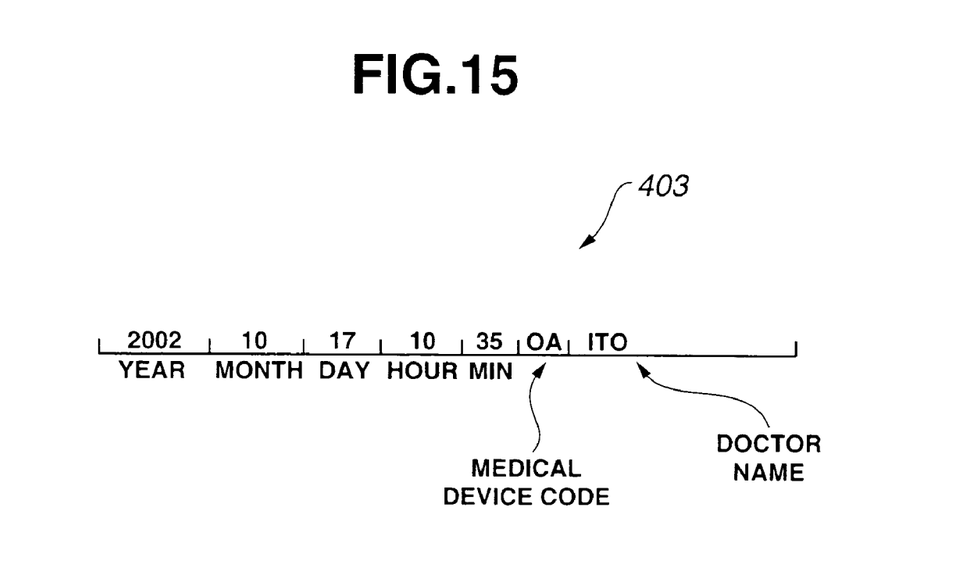
FIG. 15 is an explanatory diagram showing the data structure of ordering information according to the third embodiment of the present invention.

Next, a description is given of an endoscope surgery system according to a third embodiment of the present invention with reference to FIGS. 13 to 15.

Referring to FIG. 13, a system controller 320 comprises a PC board. The system controller 320 further comprises a LAN connector 361.

A hospital network 401 comprises a network board (not shown) having a LAN connector 401*a* and a LAN cable 402 connected to the network board.

The system controller 320 and the hospital network 401 connect a LAN connector 361 and a LAN connector 401*a* via the LAN cable 402.

Referring to FIG. 14, the system controller 320 comprises the above-mentioned components of the system controller 20 shown in FIG. 2 according to the first embodiment and the LAN connector 361 for connection to the hospital network 401.

Further, the system controller 320 includes, in a control unit 346, setting value storage controlling means 351, ordering information obtaining means 352, automatic setting file searching means 353, and automatic setting executing means 354.

The setting value storage controlling means 351 stores a series of setting values of the connected medical devices by using a doctor name of the operation, into the hard disk 48 as an automatic setting file.

The ordering information obtaining means 352 accesses the hospital network 402 upon turning on the system controller 320, and obtains its ordering information.

The automatic setting file searching means 353 selects the doctor name from the obtained ordering information, and searches for the automatic setting file of the hard disk 48 based on the doctor name.

When the automatic setting file searching means 353 hits the automatic setting file, the automatic setting executing means 354 executes the automatic setting of the hit automatic setting file.

Conventionally, the automatic setting of the medical devices is performed by a nurse who prepares for it. Recently, many hospitals have the LAN for setting the schedule for the medical devices and the doctor schedule. In particular, the schedule of the medical devices takes root as an ordering system.

According to the ordering system, it is known when and where, who of the doctor uses the medical device.

Referring to FIG. 15, a data structure 403 of the ordering information comprises date, using time, using medical device, and doctor name.

The power supply of the system controller 320 is turned on, then, the system controller 320 accesses the hospital network 401, and it obtains the ordering information.

The ordering information includes that of another medical device. However, the operator's device can be recognized based on a device ID. The ordering information has the doctor name and can easily be obtained.

The system controller 320 compares the thus-obtained doctor name with the name of the automatic setting data recorded in the hard disk 48. If the obtained doctor name matches the name in the automatic setting data, the system controller 320 executes the automatic setting of the automatic setting data of the name. If the doctor name does not match the name in the automatic setting data, the system controller 320 performs no operation.

According to the third embodiment, the system controller 320 only reads the ordering information, thereby completing the automatic setting of the medical devices. Thus, the troublesomeness for setting the medical devices is removed and, further, the medical device can be operated in accordance with the ordering. The arrangement time of the medical devices is reduced and the medical devices are available in a short time.

Next, a description is given of an endoscope surgery system according to a fourth embodiment with reference to FIGS. 1, 2, 11, and 12.

In the description of the fourth embodiment, FIG. 11 is a block diagram showing a main portion of a system controller of the endoscope surgery system and FIG. 12 is an explanatory diagram showing a play screen of a video scope of the VTR. Components (not shown in FIG. 11) in the endoscope surgery system will be described with reference to FIGS. 1 and 2.

Referring to FIG. 11, according to the fourth embodiment, operation log recording controlling means 251 records the operation of the medical devices as the operation log file into the hard disk 48.

The recording start and the recording stop of the VTR 17 are recorded to the operation log file.

When the error is caused in the medical devices, error log recording controlling means 252 records the error contents as an error log file into the hard disk 48.

The VTR play controlling means 254 plays the VTR 17 (refer to FIGS. 1 and 2) based on the data from the control signal receiving unit 41.

Upon playing the VTR 17, the display control means 255 reads a timer counter value of the VTR 17, counts the play time of the VTR 17, calculates the time, and displays, on the monitor 18 (refer to FIGS. 1 and 2) or the display panel 22 (refer to FIGS. 1 and 2), information recorded to the operation log file or the error log file in the hard disk 48 in accordance with the generating timing of the information, simultaneously with the generation of the VTR 17 image.

With the above structure, when the state of the medical device changes, the operation log recording controlling means 251, the error log recording controlling means 252, and the hard disk 48 are state change recording means which records, to the log file, change information and the occurrence time of the state change.

The VTR 17 is recording means which records the endoscope image.

The VTR play controlling means 254 is play and display means which plays and displays the video image recorded to the recording medium of the VTR 17 (recording means) to the monitor 18 or the display panel 22.

The display control means 255 includes the play counting means, the calculating means, and the log contents display means.

The play counting means of the display control means 255 counts the play time of the play and display means.

The calculating means of the display control means 255 reads the recording start time of the operation log file and a timer counter value of the VTR 17, matches the read counter value to the play counting time of the play counting means, and calculates the actual play time.

The log contents display means of the display control means 255 compares the actual play time calculated by the calculating means with the occurrence time of the operation log file, and displays the log contents at the occurrence time simultaneous with the play time.

According to the fourth embodiment, the operation log and the error log are displayed together with the endoscope image, thereby easily using the system. The medical devices are directly operated or are operated via the operation panel 21 and, thus, the information is transmitted to the system controller 220. The operation log recording controlling means 251 in the control unit 246 records the information as the operation log file in the hard disk 48 in the system controller 220. Similarly to the recording of the operation log file, when the error is caused in the medical device, such error information is recorded as the error log file in the hard disk 48 in the system controller 220.

The endoscope image during the operation is generally recorded to the VTR 17. Upon starting to record the data of the VTR 17, the start time and the end time are recorded and are stored in the operation log file.

The stored video tape is played and then the screen 260 shown in FIG. 12 is displayed on the monitor 18 or the display panel 22.

The screen 260 comprises a play area 261 of the recording image of the VTR 17 and the display area 262 for the operation log and the error log. The VTR 17 is played, the recording start time for recording the data to the operation log file and the timer counter value of the VTR are read to the calculating means of the display control means 255, and the play counting means starts the play counting operation of the VTR 17. The display control means 255 calculates the actual play time based on the start time, the timer counter value, and the play counting time.

The log contents display means of the display control means 255 searches the operation log and the error log in the hard disk 48 from the actual play time, and displays the index recorded to the corresponding operation log and error log on the display area 262 for the operation log and the error log.

According to the fourth embodiment, the operation log, the error log, and the endoscope image are displayed together, thereby easily displaying the information on the operation situation and the error occurrence. Thus, the device failure is easily analyzed and, further, the operation of the operator is easily analyzed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical system comprising:
   a first medical device used for a first medical action, the first medical device including an image pickup device;
   a second medical device used for a second medical action that is different from the first medical action;
   a state information recording unit which, when a change in setting of or an operation for driving or an error of at least one of the first medical device and the second medical device changes is informed records information related to the contents thereof and the occurrence time of the information;
   an image recording unit for recording an image obtained from the image pickup device and a time to have started the recording of the image;
   a play and display unit which plays and displays the image recorded in the image recording unit; and
   a display control unit for playing the information recorded in the state information recording unit on the play and display unit in compliance with the playing and displaying of the image recorded in the image recording unit, the display control unit displaying the information of the operation at the occurrence time corresponding to the time of having recorded the image that is played and displayed on the play and display unit by comparing the time to have started the recording of the image recorded in the image recording unit and the occurrence time of the information recorded in the state information recording unit in case where the image recorded in the image recording unit is again played and displayed on the play and display unit after recording.

2. A medical system according to claim 1, wherein the display control unit, when the image recorded in the image recording unit is again played and displayed on the play and display unit after recording, reads the recording start time recorded in the image recording unit and counts the play and display time, and adds the recording start time and the play and display time to calculate the time to have recorded the played and displayed image and compares the calculated recorded time with the occurrence time of the state information recorded in the state information recording unit, thereby to display the state information at the occurrence time corresponding to the time to have recorded the played and displayed image on the play and display unit.

3. A medical system according to claim 1, wherein the first medical device is an endoscope device including an image pickup device and an illuminating device, and
   the second medical device is a treating device having a treating function to treat living tissues.

4. A medical system according to claim 3, wherein the display control unit, when the image recorded in the image recording unit is again played and displayed on the play and display unit after recording, reads the recording start time recorded in the image recording unit and counts the play and display time, and adds the recoding start time and the play and display time to calculate the time to have recorded the played and displayed image and compares the calculated recorded time with the occurrence time of the state information recorded in the state information recording unit, thereby to display the state information at the occurrence time corresponding to the time to have recorded the played and displayed image on the play and display unit.

* * * * *